United States Patent [19]
Chaudhuri et al.

[11] Patent Number: 5,451,394
[45] Date of Patent: Sep. 19, 1995

[54] QUATERNARY SALTS OF PARA-DIALKYLAMINO BENZAMIDE DERIVATIVES

[75] Inventors: Ratan K. Chaudhuri, Butler; Anatoly Alexander, Berkeley Heights; Anna A. Gripp, Whippany, all of N.J.

[73] Assignee: ISP Van Dyk Inc., Belleville, N.J.

[21] Appl. No.: 111,690

[22] Filed: Aug. 25, 1993

[51] Int. Cl.$^6$ .................. C07D 249/00; C07C 233/77; A61K 7/06; A61K 7/42
[52] U.S. Cl. ........................ 424/60; 424/47; 424/70.9; 514/938; 544/58.1; 544/165; 546/221; 546/233; 548/146; 548/215; 548/567; 564/163
[58] Field of Search ......... 548/567; 564/163; 514/938; 424/47, 70, 60, ; 546/229

[56] References Cited
PUBLICATIONS

The Merck Index, 10th Ed., (1983), p. 1116, item 7658.
Steen, et al., C.A.; 118:51841 (1992).
Kimura, et al., C.A.; 109:31538 (1988).
Schanker, et al., C.A.; 104:61509 (1986).
Eaton, et al., C.A.; 89:208889 (1978).

*Primary Examiner*—Joseph Paul Brust
*Attorney, Agent, or Firm*—Marilyn J. Maue; Joshua J. Ward

[57] ABSTRACT

This invention relates to non-hydrolyzable, non-irritating, hair, skin and textile substantive quaternary ammonium salts of a para-dialkylamino benzamide having the formula

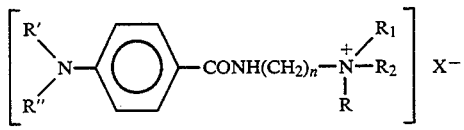

wherein R' and R" are each selected from the group of $C_1$ to $C_2$ alkyl; n is an integer having a value of from 2 to 6; R is an alkyl radical having from 1 to 30 carbon atoms; $R_1$ and $R_2$ are each selected from the group of $C_1$ to $C_4$ alkyl, hydrogen and, alternatively, $R_1$ and $R_2$, together with the attached cationic nitrogen atom can form a 5 to 6-membered heterocyclic ring selected from the group of

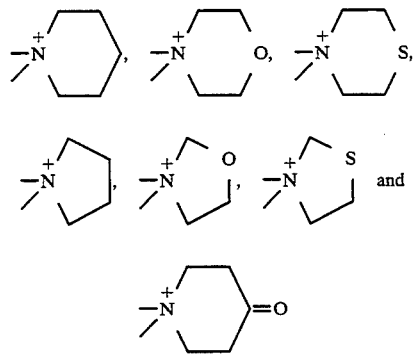

and X is an anion. These benzamide derivatives are active sunscreening agents which are usefully employed at a concentration of from about 0.5 to about 10 wt. % in a formulation requiring protection against the harmful effects of sunlight, such as skin burn, hair damage, color fading, etc.

13 Claims, No Drawings

QUATERNARY SALTS OF PARA-DIALKYLAMINO BENZAMIDE DERIVATIVES

In one aspect the present invention relates to novel substantive compounds for skin, hair, paints, textiles and fibers of wool, cotton, silk and synthetics which provide protection from the undesirable affects of sunlight. In another aspect the invention relates to the use of such compounds as sunscreens in personal care or in other formulations.

BACKGROUND OF THE INVENTION

In addition to the recognized detrimental affects of sunlight on printed or colored fabrics and painted surfaces, human hair damage caused by sunlight in the ultraviolet spectrum is more severe than that resulting from all other factors such as weather, wind, atmospheric pollution, salt water, chlorinated water, perming, coloring, bleaching and improperly applied or repetitive treatments. Notwithstanding the need for effective sunscreens, none have been developed which provide desired hair substantivity while avoiding other deleterious changes in structure, brittleness, hair softness and the like. Prior attempts to remedy these problems have proven unsatisfactory. For example, U.S. Pat. Nos. 3,879,443; 3,878,229; 4,069,309 and 4,680,144 disclose various sunscreens dependent on an ester functionality. However, these compounds tend to be hydrolytically unstable to the extent that the formulator must avoid hydrolysis conditions during formulation. Also, since these esters lack hydrogen bonding capability with skin protein or hair keratin, they are deficient in hair substantivity.

U.S. Pat. No. 4,256,664 proposes several p-substituted aromatic amines or nitro containing sunscreens having an amide functionality and optionally containing a hydroxy substituent. However, the primary amines of this patent oxidize rapidly in air, thereby altering desired hair color and, in some instances, form nitroso amines which are known carcinogens. Additionally, the primary amines and nitro compounds are recognized skin irritants. Further, the amine compounds are subject to intermolecular and solvent hydrogen bonding which characteristic causes a significant shift in UV maxima absorption and reduces absorption in the desired spectrum range.

M. F. Saettone et al. in THE INTERNATIONAL JOURNAL OF COSMETIC SCIENCE, Vol. 8, 9–25, 1986, describes types of amido quaternaries based on salicyclic and cinnamic acids. The salicylamides are ortho substituted with spatial arrangements permitting internal molecular hydrogen bonding. The ortho relationship of the phenolic group to the bulky amide group causes crowding and stress within the molecule. To counter this steric effect, the groups which deviate slightly from planarity are present. However, any minor deviation from planarity causes a reduction in the extinction coefficient and hence a corresponding reduction in the efficacy of protection against harmful sun rays. On the other hand, cinnamoylamides have additional unsaturation and conjugation with respect to both the aromatic ring and the carbonyl group. This structure permits electron delocalization to take place within the molecule; but, although the energy corresponding to this electron transition corresponds to a desired wavelength of about 305 nm, the molar extinction coefficient is materially lower than that for the corresponding para-dimethylamino carbonyl analog. Finally, the cinnamoyl compounds are subject to cis-trans isomerization as well as to polymerization, i.e. characteristics to be avoided for effective sunscreens.

Still another patent, U.S. Pat. No. 4,061,730, seeks to remedy the above problems by the use of quaternized benzylidene camphor sunscreens. However, since quaternization eliminates conjugation in the compound, the sun protection capability is significantly reduced.

From the above discussion, it will be appreciated that the discovery of a commercially viable and hair substantive sunscreen is remote.

Accordingly, it is an object of the present invention to provide an effective, non-irritating sunscreening agent which is not subject to hydrolysis, and which has high substrate substantivity.

Another object of the invention resides in the synthesis of said sunscreening agent.

Still another object is to provide a novel water insoluble sunscreening agent for extended use in hair care.

These and other objects will become apparent from the following description and disclosure.

THE INVENTION

In accordance with the present invention, a substantially water insoluble, non-irritating and hydrolysis resistant cationic sunscreening agent is provided which possesses high molecular planarity and which is easily incorporated into commercial formulations to provide stable compositions.

The present benzamide derivatives can be employed to prevent color alteration in paints or painted substrates, e.g. automotive vehicles and mono or multi colored textile fabrics, and the like. Because of their high hair, skin and wool substantivity, the present compounds are particularly useful in cosmetic applications, as in hair conditioning shampoos, silicone containing softeners, hair conditioners and rinses, styling mousses, gels or lotions, hair sprays, hair dyes and bleaching compositions. Since the present compounds interact with hair protein, they provide UV protection and conditioning properties long after hair treatment. Beneficial cosmetic applications also include their compatability and easy incorporation into skin care compositions, such as sun protection creams and lotions to inhibit skin ageing, wrinkle formation, erythema and carcinogenesis as well as in nail polish, lipstick, rouge or make-up bases. The benzamide derivatives of this invention also reduce fading of natural and synthetic dyes and minimize or eliminate photodegradation in dyed and undyed cotton, linen, silk and wool fabrics as well as color alteration in paints and painted surfaces exposed to climatic conditions as in automotive and house paints.

The non-hydrolyzable, non-irritating, substantive derivatives of this invention are quaternary ammonium salts of a para-dialkylamino benzamide compound having the formula

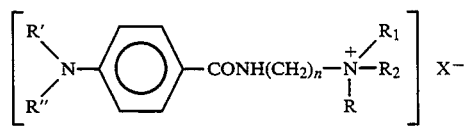

wherein R' and R" are each selected from the group of $C_1$ to $C_2$ alkyl; n is an integer having a value of from 2 to 6; R is a linear, branched or cyclic alkyl radical having from 1 to 30 carbon atoms; $R_1$ and $R_2$ are each selected from the group of $C_1$ to $C_4$ alkyl, hydrogen and, alternatively, $R_1$ and $R_2$, together with the attached cationic nitrogen atom can form a 5 to 6-membered heterocyclic ring selected from the group of

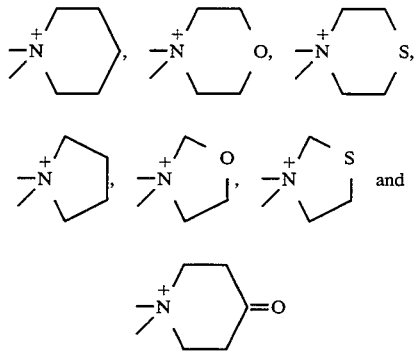

and X is an anion, preferably selected from the group of chloride, bromide, sulfate, sulfonate, haloacetal and aryl sulfonates.

Of the above benzamide compounds, preferred are those wherein n has a value of 2 to 4; R is alkyl having 12 to 18 carbon atoms and $R_1$ and $R_2$ are each alkyl having from 1 to 4 carbon atoms. It is to be understood that mixtures of the present benzamides can be employed in a composition to provide combined UV protection.

The present compounds are unique in that they absorb UV in wavelengths of from about 280 to about 330 nm and possess a molecular extinction coefficient of up to about 30,000. The present compounds are generally compatible with any composition requiring UV protection and can be added in an effective amount of between about 0.5 and about 10 wt. %, preferably between about 1 and about 3 wt. %, based on total composition.

Solutions of the present compounds are also usefully applied as a separate coating over a treated substrate. For example, a vehicle or aircraft can be sprayed or brushed, with a 2 to 10% solution of the present compound dissolved in a suitable solvent such as fatty alcohols, e.g. octyldodecanol, isocetyl alcohol, alkyl lactates containing 12 to 18 carbon atoms, 2-ethylhexyl p-dimethylamino benzoate (Padimate O), etc. The compound can also be pressed into a cosmetic cake as in a cake powder for application to the skin.

The benzamides of the present invention are easily synthesized according to the following two-stage reaction

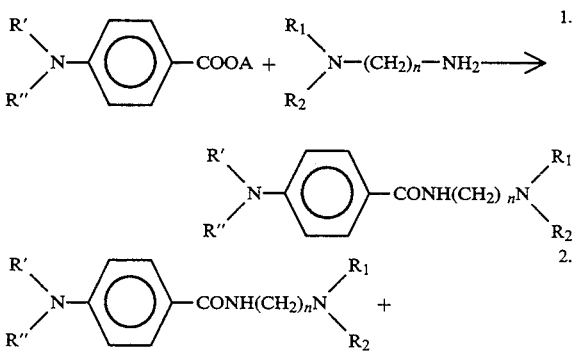

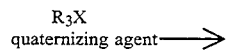

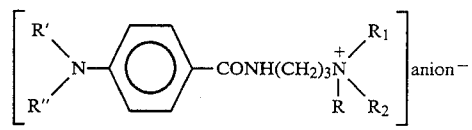

wherein A is $C_1$ to $C_8$ alkyl and $R_3$ is halo or an organic moiety, e.g. aryl such as tolyl.

Stage 1 of the reaction is carried out at a temperature of between about 110° and about 180° C., preferably under reflux conditions for continuous removal of the alkanol by-product. The reaction of the aminobenzoate with diamine is conducted in the presence of a base catalyst such as dimethyl formamide, triethanol amine, N-methyl-morpholine, hexamethylene tetraamine, dimethylamino-2-hydroxy propane, 2,4,6-tris(dimethylaminomethyl)phenol, potassium t-butoxide, KOH, NaOH, $NaOCH_3$, $NaOC_2H_5$ and the like. Between about 0.5 and about 24 hours, in the presence of from about 0.5 to about 2 weight % of the base catalyst, is sufficient to complete the reaction to the aminobenzamide product in a high yield greater than 96%. Preferred conditions for this stage of the reaction include a temperature of from about 120° to about 170° C. for a period of between about 1 and about 2 hours. The aminobenzoate and diamine can be reacted as a melt or in a 15-50%, preferably a 20-30%, solids solution or emulsion in a suitable liquid medium provided by, e.g. acetone, methyl ethyl ketone, ethyl acetate, cyclohexane, octane, xylene, toluene, etc. and mixtures thereof. Also, the reaction can be effected under a pressure sufficient to maintain a liquid phase when needed.

The quaternization stage is carried out at a temperature of between about 70° and about 140° C., preferably between 100° and 130° C., and is completed within a period of from about 10 minutes to about 24 hours, more often 1 to 6 hours, after which the product can be recovered by crystallization, from ethyl acetate or a similar solvent. Although the product can be recovered in crystalline form, these crystals may contain up to 10 wt. % water, more desirably between about 1 and about 8 wt. % water.

The quaternizing agents employed in the present invention include $C_1$ to $C_{30}$ alkyl- halide, sulfate, sulfonate, acetal and aryl sulfonates, e.g. p-tolyl sulfonate. The alkyl moiety of the quaternizing agent can be substituted with halogen and can be branched or linear. Preferred quaternizing agents are those containing from 12 to 20 carbon atoms in the alkyl moiety.

In the above reactions, equimolar amounts of the reacting species are preferred; however, ratios of from about 1:2 to about 2:1 may be employed in the second stage reaction.

Advantages of the present sunscreening agents are derived from the aromatic —$N(R)_2$ group, which unlike —$NH_2$, is stable, is not sensitive to pH changes present in various formulations, and is not oxidized in air. The substitution of —$N(R)_2$ in the para-position on the phenyl ring also eliminates H bonding with protic solvents which characterize the ortho —OH and —$NH_2$ phenyl substitutions of other sunscreens while the replacement of the ester linkage found in prior compounds with an amide linkage provides an additional binding site for the hair protein (keratin) through H-bonding. The presence of the quaternary amine group provides the salt linkage through the electrovalent union of the side chain acid keratin residues thereby imparting conditioning properties. All of the above factors in combination provide the synergistic effects and benefits of the present sunscreens.

Formulations containing the present quaternized amino-benzamide compounds can be used in pump or aerosol sprays.

The cosmetic formulations incorporating the present sunscreens generally include between about 40 and about 90 wt. % of a carrier or propellant such as deionized water, alcohol, isobutane or propane, etc., between about 10 and about 40 wt. % of a surfactant or surfactant mixture such as sodium and/or ammonium, lauryl sulfate, sodium laureth sulfate etc., and fragrance and/or coloring agent as desired.

These formulations may optionally contain between about 5 and about 50 % of one or more inert components including a film forming polymer such as a $C_1$ to $C_4$ ester of a methyl vinyl ether/maleic anhydride copolymer, a vinyl pyrrolidone/vinyl acetate copolymer, etc.; a preservative such as bronopol, an ester of p-hydroxybenzoic acid, 2-methyl-3(2H) isothiazolone, a mixture of methyl and propyl paraben, dimethyl-5,5-dimethylhydantoin, Germall® 115, imidazolidinyl urea, etc.; a sequestrant, and an antistatic agent.

Following compilation of formulations serves to illustrate the diversity of formula types currently available in the marketplace. In each of the formulations the sunscreen of the present invention is employed.

A. Formula type: FACE CREAM

| Ingredients | % w/w |
|---|---|
| Phase A | |
| Benzophenone-3 | 8.0 |
| Sunscreen | 6.0 |
| Cyclomethicone | 10.0 |
| Glyceryl stearate SE | 5.0 |
| Phenyldimethicone | 2.0 |
| Cetearyl alcohol (and) ceteareth-20 | 2.0 |
| Cetyl alcohol | 1.0 |
| Octyl palmitate | 10.0 |
| Phase B | |
| Water | QS |
| Preservative | QS |
| Glycerine | 5.0 |
| Diethanolamine p-methoxycinnamate | 8.0 |
| Titanium dioxide | 3.0 |
| Xanthan | 0.2 |
| Hydroxyethylcellulose | 0.1 |
| Phase C | |
| Fragrance | 0.3 |

B. Formula type: w/o WATER-RESISTANT CREAM

| Ingredients | % w/w |
|---|---|
| Phase A | |
| Mineral oil (and) lanolin alcohol | 5.0 |
| Isopropyl palmitate | 10.0 |
| Beeswax | 8.0 |
| Sorbitan sesquioleate | 2.0 |
| Mineral oil | 25.0 |
| Sunscreen | 6.0 |
| Benzophenone-3 | 4.0 |
| Phase B | |
| Water | QS |
| Borax | 0.4 |
| Preservative | QS |
| Propylene glycol | 5.0 |
| Phase C | |
| Fragrance | 0.25 |

C. Formula type: SUN BLOCK CREAM

| Ingredient | % w/w |
|---|---|
| Phase A | |
| Isopropyl myristate | 9.0 |
| Sunscreen | 10.0 |
| Benzophenone-3 | 5.0 |
| Menthyl anthranilate | 5.0 |
| Stearic acid XXX | 5.0 |
| Glyceryl monostearate | 6.0 |
| Cetyl alcohol | 5.0 |
| PEG-40 stearate | 2.0 |
| Phase B | |
| Water | QS |
| Xanthan | 0.3 |
| DEA-cetyl phosphate | 8.0 |
| Preservative | QS |
| Glycerine | 3.5 |
| Phase C | |
| Fragrance | 0.25 |

D. Formula type: WATER-PROOF LOTION

Expected SPF: 15

| Ingredient | % w/w |
|---|---|
| Phase A | |
| Sunscreen | 8.0 |
| Benzophenone-3 | 4.0 |
| Myristyl myristate | 1.0 |
| Propylene glycol dipelargonate | 5.0 |
| Steareth-20 | 1.0 |
| Phase B | |
| Water | QS |
| Carbomer 1342 | 0.2 |
| Preservative | QS |
| Propylene glycol | 5.0 |
| Phase C | |
| PEG-15 cocamine | 0.2 |
| Phase D | |
| Fragrance | 0.25 |

E. Formula type: CATIONIC SUNSCREEN LOTION

| Ingredient | % w/w |
|---|---|
| Phase A | |
| Glycol stearate | 5.0 |
| $C_{12-15}$ alcohols benzoate | 3.5 |
| Sunscreen | 5.0 |
| PEG-40 stearate | 1.5 |
| Phase B | |
| Water | QS |
| Preservative | QS |
| Stearamidopropyl PG-dimonium chloride Phosphate | 3.5 |
| Glycerine | 4.0 |
| Phase C | |
| Fragrance | 0.3 |

F. Formula type GREASELESS SUNSCREEN OIL

| Ingredient | % w/w |
|---|---|
| Benzophenone-3 | 3.0 |

-continued

F. Formula type GREASELESS SUNSCREEN OIL

| Ingredient | % w/w |
|---|---|
| Sunscreen | 7.0 |
| Mineral Oil | QS |
| Octyl palmitate | 15.0 |
| Fragrance | 0.3 |
| Sesame Oil | 1.0 |
| BHA | 0.1 |

G. Formula type: SUNSCREEN OIL
Comments: Octyl palmitate reduces oiliness of mineral oil while minimizing UV curve shift
Expected SPF: 3

| Ingredient | % w/w |
|---|---|
| Sunscreen | 4.0 |
| Octyl palmitate | QS |
| Lauryl lactate | 15.0 |
| Mineral oil | 35.0 |
| Isocetyl alcohol | 10.0 |
| Fragrance | 1.0 |

H. Formula type: LIP BALM STICK

| Ingredient | % w/w |
|---|---|
| Sunscreen | 7.0 |
| Benzophenone-3 | 3.0 |
| Castor oil | QS |
| Octyldodecanol | 5.0 |
| Beeswax | 15.0 |
| Ozokerite | 6.0 |
| Myristyl lactate | 4.0 |
| Candililla wax | 6.0 |
| Petrolatum | 5.0 |
| Fragrance | 0.5 |

I. Formula type: Water-resistant sunscreen mousse

| Ingredient | % w/w |
|---|---|
| Phase A | |
| Dimethicone | 10.0 |
| Sunscreen | 3.5 |
| Benzophenone-3 | 3.0 |
| Glyceryl PABA | 3.0 |
| Stearic acid XXX | 4.0 |
| Cetyl alcohol | 0.5 |
| Vitamin E acetate | 0.1 |
| Phase B | |
| Water | QS |
| Hydroxypropyl cellulose | 0.5 |
| Triethanolamine 99% | 0.5 |
| Ethanol | 20.0 |
| Preservative | QS |

J. Formula type: Sunscreen mousse

| Ingredient | % w/w |
|---|---|
| Water | QS |
| Propylene glycol | 5.0 |
| Quaternium-26 | 3.0 |
| Octyl methoxy cinnamate | 3.0 |
| Cetearyl alcohol (and) ceteareth-20 | 1.0 |
| Octyldodecanol | 5.0 |
| Preservative | QS |

K. Formula type: MAKE-UP MOUSSE

| Ingredient | % w/w |
|---|---|
| Phase A | |
| Glyceryl dilaurate | 2.5 |
| Glyceryl stearate SE | 3.0 |
| Cetyl alcohol | 1.5 |
| Decyl oleate | 2.5 |
| Propylene glycol depelargonate | 3.0 |
| Sunscreen | 3.5 |
| Phase B | |
| Water | QS |
| Hydroxyethylcellulose | 0.5 |
| Sorbitol 70% | 5.0 |
| Pigment | 15.0 |
| Preservative | QS |
| Phase C | |
| Ethanol | 20.0 |

L. Formula type: SUNSCREEN GELEE

| Ingredient | % w/w |
|---|---|
| Myristyl lactate | 5.0 |
| Tridecylneopentanoate | 10.0 |
| Sunscreen | 4.0 |
| Petrolatum | QS |
| Paraffin | 5.0 |
| Beeswax | 4.0 |
| Calcium stearate | 5.0 |
| Cetearyl alcohol | 2.0 |
| Fragrance | 1.0 |
| Preservative | QS |

M. Shampoo

| | Parts |
|---|---|
| Emersol 6400 (sodium lauryl sulfate) | 30.0 |
| Rewomid DC-212/S (Cocamide DEA) | 5.0 |
| Deionized water | 60 |
| Preservative | QS |
| Sunscreen | 4 |

Preparation: Heat all ingredients to 45–50° C.; cool to room temperature

N. Cream Rinse

| | | |
|---|---|---|
| A. | Stearalkonium chloride (50% solids) | 1.5 |
| | Sodium chloride | 0.1 |
| | Deionized water | 90.9 |
| | Sunscreen | 3.0 |
| B. | Emerest 2642 (polyethylene glycol 8 distearate) | 1.5 |
| | Ethoxyol AC (laneth-10 acetate) | 2.0 |
| | Preservative | |

Preparation: Heat both phases to 70° C.; add A to B; cool to room temperature

O. Conditioning Shampoo Formulation, taken from Example 7 of U.S. Pat. No. 5,078,990, which are incorporated herein as representative teachings of suitable formulations for addition of the present sunscreens.

| ITEM | COMPONENT | WT. 5 |
|---|---|---|
| 1 | ammonium lauryl sulfate | 6.0 |
| 2 | ammonium laureth sulfate (1 mole EO) | 9.45 |
| 3 | sodium lauryl sulfate | 4.5 |
| 4 | distearyl dimethyl ammonium chloride (AROSURF ®) | 0.3 |
| 5 | distearyl phthalamic acid | 3.5 |
| 6 | sodium hydroxide | 0.085 |
| 7 | FD & C Blue #1 | 0.00024 |
| 8 | D & C yellow #10 | 0.0012 |

-continued

| | O. Conditioning Shampoo Formulation, taken from Example 7 of U.S. Pat. No. 5,078,990, which are incorporated herein as representative teachings of suitable formulations for addition of the present sunscreens. | |
|---|---|---|
| ITEM | COMPONENT | WT. 5 |
| 9 | tetrasodium EDTA/water softener | 0.2 |
| 10 | fragrance | 0.5 |
| 11 | DMDM hydantoin (GLYDANT ®) preservative | 0.1 |
| 12 | methyl & methylchloro isothiazolinone-preservatives | 0.05 |
| 13 | 33% SE-30 polysiloxane gum/67% SF96-350 polysiloxane oil | 2.5 |
| 14 | sunscreen | 0.8 |
| 15 | soft water | QS to 100 |

Add items #1, #2, and #3 and begin heating batch to 180° F.–185° F.
At 180° F. add item #4 and allow to completely mix in.
Add items #5, allow to mix in.
Add item #6, #7, and #8.
Allow to mix for 30 minutes at 180° F.–185° F.
After this time, samples should be cooled with Item #15.

The conditioning agent (item 13) and sunscreen (14) then are added and mixed at a temperature of at least 30° C. and preferably at 40° C. to 50° C. The composition at this point exhibits lower frequency stretching bands at the higher temperatures and the conditioning agent is easily dispersed or dissolved within the emulsion without separation.

| Automotive Acrylic Enamel | |
|---|---|
| Components | wt. % |
| TiO$_2$ base containing 60% pigment | 220 |
| Color tinting base | 40 |
| Acrylic polymer (with pendant —OH and —COOH groups) 55% solids | 350 |
| Butoxy methylol melamine-formaldehyde resin-55% solids | 230 |
| Butyl alcohol | 37 |
| Toluene sulfonic acid 50% in xylene | 2.6 |
| Xylene | 75.0 |
| Sunscreen | 5.4 |
| Propylene glycol methyl ether acetate | 40.0 |
| | 100.00 |
| Total solids | 45 wt. % |
| Pigment solids | 25 wt. % |
| Crosslinker of polymer | 30% |

| White Aircraft TopCoat | wt. % |
|---|---|
| 1:1 Aliphatic isocyanate-polyester polyol resin | 20.0 |
| TiO$_2$ (R960 Exterior grade) | 16.0 |
| Urethane catalyst | 2.0 |
| Flow/leveling/flood and float additives | 2.0 |
| Sunscreen | 10.0 |
| Mixture of methyl ethyl ketone, methyl isobutyl ketone and methyl allyl ketone | 50.0 |

Having generally described the invention, reference is now had to the accompanying Examples which illustrate preferred embodiments but which are not to be construed as limiting to the scope of the invention as more broadly defined above and in the appended claims.

EXAMPLE 1

Preparation of N-(3-Dimethylaminopropyl)p-dimethylamino benzamide

Ethyl-p-dimethylaminobenzoate (164.9 g, 0.85 mole), 3-dimethylaminopropylamine (95.9 g, 0.94 mole) and sodium methoxide (2.8 g, 0.054 mole) were introduced into a 4-neck, 500 ml glass reactor, equipped with stirrer, heater, nitrogen purge and deflegmator with a Dean-Stark device. The charged reactor was flushed with dry nitrogen for 15 minutes at ambient temperature and was then heated to 150° C. under vigorous stirring. After about 15 minutes accumulation of distillate, the reactor temperature was gradually increased to 180° C. in 5° increments over a period of I hour and was then maintained at 180° C. for an additional hour, whereupon a sample of the product, analyzed by glass chromatography (GC) indicated 99+% conversion of the ester.

The resulting mixture was then cooled to 95° C. and washed twice with 200 ml of hot water after which the aqueous phase was cooled to room temperature and precipitated crystals recovered by filtration. These crystals were then combined with the organic phase in the reactor.

A vacuum of about 10–20 mm Hg was then applied to the product in the reactor which was heated to 90°–95° C. for 30 minutes. The resulting distillate containing water and light products was discarded. The residue was cooled to room temperature and was identified by elemental analysis, $^1$H and $^{13}$NMR and FTIR spectra, as N-(3-dimethylamino-propyl)-p-dimethylaminobenzamide. The product yield was 205 g (96.9% of theoretical based on ethyl-p-dimethylamino-benzoate).

EXAMPLE 2

Preparation of Stearyl-[3-(p-dimethylaminobenzamido) propyl]-Dimethylammonium p-toluenesulfonate N-(3-dimethylaminopropyl)-p-dimethylaminobenzamide (77 g, 0.31 mole) from Example 1 and 131.5 g of stearyl-p-toluenesulfonate (0.31 mole) was heated to 110° C. under a blanket of nitrogen with continuous stirring for 2 hours. The resulting melt was dissolved in 800 ml of hot ethylacetate and then crystallized by cooling to ambient temperature. The crystals were recovered by filtration, dried in air and then under vacuum at 50°–60° C. The resulting whitish crystals of stearyl-[3-(p-dimethyl-aminobenzamido)propyl]-dimethyl ammonium p-toluenesulfonate were found to have a melting point of 122°–125° C. and the yield 191.8 g, was 92% of theoretical. The structure and purity of the product were confirmed by elemental analysis, NMR, FTIR and UV spectra.

EXAMPLE 3

Preparation of Hexadecyl-[3-p-dimethylaminobenzamido)propyl]-dimethxlammonium p-toluenesulfonate The synthesis as described in Example 2 was repeated except that 122.8 g of hexadecyl-p-toluene sulfonate (0.31 mole) was used as the quaternizing agent. The quaternized product yield was 181.8 g (91% of theoretical).

EXAMPLE 4

Preparation of
Dodecyl-[3-(p-dimethylaminobenzamido)propyl]-dimethylammonium p-toluenesulfonate The synthesis as described in Example 2 was repeated except that 105.4 g of dodecyl-p-toluene sulfonate (0.31 mole) was used as the quaternizing agent and the quaternized product was crystallized from 1000 ml of methylethylketone. The yield was 149.6 g (82% of theoretical).

EXAMPLE 5

Preparation of
(Cetylstearyl)-[3-(p-dimethylaminobenzamido)propyl]-dimethylammonium p-toluenesulfonate The synthesis as described in Example 2 was repeated, except that 125.6 g of cetylstearyl-p-toluene sulfonate (0.31 mole) was used as the quaternizing agent and the resulting melt was flaked without crystallization.

EXAMPLE 6

Preparation of
(Myristylacetyl)[3-(p-dimethylaminobenzamido)]dimethylammonium chloride The synthesis described in Example 2 was repeated except that 17.5 g (0.07 mole) of the amide synthesized in Example 1 was employed and 20.4 g (0.07 mole) of myristyl chloroacetate (0.07 mole) was used as the quaternizing agent. The quaternized product, 12.3 g (32% of theoretical) was crystallized from 100 ml of methylethylketone. Additional product was obtained by concentrating the filtrate followed by crystallization.

EXAMPLE 7

Preparation of
N-(2-N-Morpholinoethy)p-dimethylamino benzamide

Ethyl-p-dimethylaminobenzoate (30.9 g, 0.16 mole), N-aminoethylmorfoline (25 g, 0.19 mole) and sodium methoxide (0.6 g) were introduced into a 3-neck, 100 ml glass reactor, equipped with stirrer, heater, nitrogen purge and deflegmator with a Dean-Stark device. The charged reactor was flushed with dry nitrogen for 15 minutes at ambient temperature and was then heated to 150° C. under vigorous stirring. After about 15 minutes accumulation of distillate, the reactor temperature was gradually increased to 170° C. in 5° increments over a period of 1 hour and was then maintained at 170° C. for a 23 additional hours.

The resulting mixture was then cooled to room temperature, washed with 300 ml of water and precipitated crystals recovered by filtration. These crystals were then suspended in another 200 ml of water and 30% of HCl was added to adjust the pH to 3. The resulting slurry was filtered, and filtrate was collected and treated with a suspension of sodium carbonate to pH 11. The precipitate was filtered, washed with water and allowed to dry. The dry crude product was then dissolved in methanol, insolubles were separated by filtration, and the remaining solution was evaporated to dryness in vacuo. The product yield was 24.7 g (56% of theoretical) of 98.5% pure product having a m.p. 154°–156° C.

A vacuum of about 10–20 mm Hg was then applied to the product in the reactor which was heated to 90°–95° C. for 30 minutes. The resulting distillate containing water and light products was discarded. The residue was cooled to room temperature and was identified by elemental analysis, $^1$H and $^{13}$NMR, and FTIR spectra, as N-(2-N-morpholinoethyl)-p-dimethylaminobenzamide. The product yield was 24.7 g (56% of theoretical based on ethyl-p-dimethylamino-benzoate).

EXAMPLE 8

Preparation of Hexadecyl-[2-N (p-Dimethylamino benzamido)ethyl]morpholinium toluenesulfonate The process of Example 2 was repeated except that 13.9 g (0.05 mole) of N-(2-N-morfolinoethyl)-p-dimethylaminobenzamide from Example 7 and 19.8 g hexadecyl-p-toluenesulfonate (0.05 mole) were used, and a temperature of 120° C. was maintained for 4 hours. The resulting product was crystallized from 100 ml of methylethylketone in a yield of 13.7 g (41% of theoretical).

EXAMPLE 9

Preparation of
N-(2-N-pyrrolidinoethyl)p-dimethylaminobenzamide

The process of Example 7 was repeated except that 8.7 g aminoethylpyrrolidine (0.077 mole), 14.5 g ethyldimethylaminobenzoate (0.075 mole) and 0.25 g sodium methylate were used. The final product in a yield of 14 g (72%) was N-(2-N-pyrrolidinoethyl)-p-dimethylaminobenzamide in 98% purity.

EXAMPLE 10

Preparation of
Dodecyl-[2-N-(p-dimethylaminobenzamidolethyl]-pyrrolidinium bromide 5.3 g of N-(2-N-pyrrolidinoethyl)-p-dimethylaminobenzamide (0.022 mole) from Example 9 and 5.0 g of dodecylbromide (0.02 mole) were heated together at 92°–94° C. for 2 hours. Product was crystallized from 80 ml of methylethylketone/methanol (8:1) mixture. The product yield was 7.8 g (86% of theoretical).

EXAMPLE 11

Preparation of
Dodecyl-[3-(p-dimethylaminobenzamido) propyl]-dimethylammonium bromide 13.2 g of N- (3-dimethylaminopropyl-p-dimethylaminobenzamide (0.05 mole) from Example 1 and 12.5 g of dodecylbromide (0.05 mole) were dissolved in 30 ml of methylethylketone and maintained at 70° C. for 8 hours. After cooling to ambient temperature the crystalline product (24 g, 93.5% of theoretical) was filtered and recovered.

EXAMPLE 12

Preparation of
Stearyl-[3-(p-Dimethylaminobenzamido)propyl]-Dimethylammonium Chloride 25.6 g of N-(3-dimethylaminopropyl)-p-dimethylaminobenzamide (0.103 mole) from Example 1 and 28.6 g of stearylchloride (0.099 mole) were melted together and kept at 130° C. for 3 hours. Product was crystallized from 250 ml of methylethylketone. Yield was 42 g (77% of theoretical yield).

EXAMPLE 13

Preparation of
Tetradecyl-[3-(p-Dimethylaminobenzamido)propyl]-Dimethylammonium Chloride 50 g of N-(3-dimethylaminopropyl)-p-dimethylaminobenzamide (0.201 mole) from Example 1 and 47 g of tetradecylchloride (0.195 mole) were melted together and kept at 130° C. for 4 hours. Product was crystallized from 250 ml of ethylacetate; the crystals were washed with another 150 ml of ethylacetate. Yield was 71 g (74% of theoretical yield).

EXAMPLE 14

Preparation of Ethyl-[3-(p-Dimethylaminobenzamido) propyl]-Dimethylammonium Toluenesulfonate 28.4 g of N-(3-dimethylaminopropyl)-p-dimethylaminobenzamide (0.114 mole) from Example 1 and 22.8 g of ethyltosylate (0.114 mole) were melted together and kept at 130° C. for 4 hours. Product was crystallized from 200 ml of methylethylketone. Yield was 42.8 g (83.5% of theoretical yield).

EXAMPLE 15

Preparation of
2-Ethylhexyl-[3-(p-Dimethylaminobenzamido) propyl]-Dimethylammonium Toluenesulfonate 21.8 g of N-(3-dimethylaminopropyl)-p-dimethylaminobenzamide (0.0875 mole) from Example 1 and 22.8 g of 2-ethylhexyltosylate (0.085 mole) were melted together and kept at 110° C. for 3 hours. Product is a highly viscous syrupy (at room temperature) liquid.

EXAMPLE 16

Demonstration of Substantivity

In order to demonstrate the substantivity and effectiveness of the present compounds to human hair, the following tests were carried out on the compounds of Examples 2, 4, 5 and 12. These were compared with benzylidene camphor para-toluene sulfonate (A) and 4-[(2-oxo-3-bornylidene)methyl]-phenyldimethyldodecylammonium para-toluene sulfonate (b) as disclosed in U.S. Pat. No. 4,061,730 and octyl-para-dimethylamino benzoate (C).

The test samples were prepared with 1 gram of human hair in a solution of 0.01% in water or isopropanol-water and using 50 ml of total solution. After standing for 2 minutes the hair was removed from the solution.

The substantivity of a sunscreening agent is determined in mg. of sunscreen absorbed/gram of hair, by substracting the absorbance at the maximum peak between 300 and 320 nm before and after dipping the hair in the solution containing the sunscreen. The results are as shown in Table I.

TABLE I

| Compound | Amount (in mg) of Sunscreen Absorbed per gm of Hair | Percentage of Sunscreen Absorbed on Hair |
| --- | --- | --- |
| Comparative A | 0 | 0 |
| Comparative B | 0 | 0 |
| 2 | 4.1 | 41 |
| 4 | 6.2 | 62 |
| 12 | 3.2 | 32 |
| 13 | 3.9 | 39 |
| 14 | 1.3 | 13 |

TABLE I-continued

| Compound | Amount (in mg) of Sunscreen Absorbed per gm of Hair | Percentage of Sunscreen Absorbed on Hair |
| --- | --- | --- |
| 15 | 2.2 | 22 |

Comparative A is methoxy cinnamate diethanol amine salt. Comparative B is 2-hydroxy-4-methoxy benzophenone-5-sulfuric acid neutralized with NaOH.

EXAMPLE 17

Demonstration of Hair Fading Reduction/Elimination

In order to demonstrate the effectiveness of the present compounds in reducing or elimination of the fading of dyed human hair, the following tests were carried out. Compounds of Examples 2, 4 and 11 were selected for this study and octyl-p-dimethylaminobenzoate (C) was used as a comparative sunscreen.

The test samples were prepared with 1 gram of dyed human hair in a solution (50 ml) of 0.01% in water or isopropanol-water. After standing for 10 minutes the hair was removed from the solution, one half was air dried, and the other half was rinsed for 5 minutes in tap water and then dried. Untreated dyed human hair was used as a control.

All test samples were irradiated with a Hanovia Ultra Violet Lamp containing a Corex D filter. It was found that at 72 hours, significant fading in both the octyl-p-dimethylaminobenzoate and control samples occurred. No fading of hair in the samples containing the sunscreens of Examples 2, 4 and 13 took place.

The rinsed samples containing 2, 4 and 13 sunscreens also retained 60 to 80% of their fade resistance.

EXAMPLE 18

Demonstration of Hair Protection Against Sun Damage

The purpose of this study was to assess the ability of the products of this invention (Examples 2 and 4) to reduce the amount of ultraviolet light-induced damage to the hair, as measured by the change in fluorescence of mercurochrome-dyed hair samples. For this study, the sunscreen compounds were each dissolved in lauryl lactate (Ceraphyl 31) at 1 and 2% (W/W) level concentration.

The procedure followed in this study involves forming a base stain solution 1% mercurochrome in 6M urea containing 0.5% of aqueous Triton X-100 * (Q.S. to 100 ml).

\* octylphenoxy octaoxahexacosan-1-ol

Degreased hair swatches are taken from 10 female subjects, 7 of which are permed or colored hair and 3 of which are virgin hair. The hair is cut $\frac{1}{4}''$ from the scalp and the proximal 3" used for study.

A first portion of the hair strands from each subject is dipped into the base stain solution to which the sunscreen solution has been added.

A second equal portion of the hair strands from each subject is dipped into the base stain solution without addition of the sunscreen solution and the first and second portions are irradiated. Finally, a third equal portion of the hair strands from each subject is untreated and used as an absolute control to determine the amount of fluorescence inherent in the hair.

Measurement of fluoroescence is carried out by mounting three hair strands of a given sample on a microscope slide cross section. A fluorescence microscope Zeiss 2FL fitted with a photomultiplier tube (PMT) EM1#9798E and a filter measures fluorescence of the strands under −600 volts supplied by a Harrison 6515A DC supplier.

The results of these tests are reported in the following Table II.

TABLE II

|  | Fluorescence Units (Average of 10 Sample Subjects) | % Decrease in Fluorescence and Control |
|---|---|---|
| Hair samples treated with Sunscreen of Example 2 (1% soln) | 16.22 | 55.61 |
| Hair samples treated with Sunscreen of Example 4 (1% soln) | 18.30 | 51.92 |
| Hair samples treated with Sunscreen of Example 2 (2% soln) | 12.10 | 68.71 |
| Hair samples treated with Sunscreen of Example 4 (2% soln) | 13.55 | 64.91 |
| Hair samples in Ceraphyl 31 solution irradiated without sunscreen | 44.89 | 30.46 |
| Hair samples irradiated in the absence of Ceraphyl 31 and/or sunscreen | 38.71 | 25.0 |

The following represent some other formulations using the sunscreen agents of this invention and illustrate their compatability with a variety of components conventionally employed in such compositions.

EXAMPLE 19

Hair Conditioner and Sunblock

The compound of Example 2 (1.0 wt. %) is premixed with 65.0 wt. % ethanol at room temperature until solution is reached. The following ingredients were then added in the order shown below with mixing between each addition.

The above formulation increases hair luster while protecting from harmful rays of the sun causing dryness.

| Component | wt. % |
|---|---|
| Lauryl lactate (ceraphyl 31) | 1.00 |
| Avocado oil | 0.05 |
| Octyl methoxycinnanamate (Escalol 557) | 1.00 |
| Deionized water | 31.45 |
| Hydrolyzed Animal Protein (Crotein SPO) | 0.25 |

EXAMPLE 20

Conditioning Hair Styling Gel and Sunscreen

Crosslinked methyl vinyl ether/maleic anhydride copolymer (6.0 wt. %) was dispersed in 80.2 wt. % of distilled water by mixing for about 45 minutes at about 87° C. The dispersion was then cooled to 60° C. and 0.4 wt. % of sodium hydroxyethyl glycinate followed by 7 wt. % of deionized water was added while cooling to room temperature.

A separate mixture of 1 wt. % polyvinylpyrrolidone in 7 wt. % deionized water was prepared at room temperature and a dispersion consisting of 1.0 wt. % compound of Example 2 and 10.0 wt. % of polyethoxylated sorbitan monolaurate (Tween 20) was added with mixing to the aqueous polyvinylpyrrolidone phase at 70° C. The resulting mixture was then added to the crosslinked copolymer phase at 70° C. and mixing was continued while cooling to 25° C.

This formulation possesses excellent hair holding power while providing subsequent use as a hair sunscreen.

EXAMPLE 21

Hair Conditioner for Dyed Hair

A dispersion of modified hydroxyethyl cellulose (0.75 wt. %) in 88.03 wt. % deionized water, 1.0 wt. % polyethoxylated sorbitan monolaurate and 0.50 wt. % phenoxyethanol was prepared at 85° C. To this dispersion was gradually added, at about 90° C., a premixed solution of 0.25 wt. % methylparaben, 0.25 wt. % propylparaben in 3.72 wt. % water. After mixing to uniformity, 2.0 wt. % glycol stearate, 1.0 wt. % mink amidopropyl dimethyl-2-hydroxyethyl ammonium chloride, 0.25 wt. % cetyl alcohol, 1.0 wt. % stearyl alcohol, 0.25 wt. % titanium dioxide on mica and 1.0 wt. % of the compound of Example 2 were added in the above order and mixed for 10 minutes and then homogenized for 10 minutes at between about 80°–90° C. The resulting uniform mixture was then cooled to room temperature. This conditioning lotion when applied to dyed hair prevents color fading upon extended exposure to the sun. Substitution of the compound of Example 4 for that of Example 2 in the above hair conditioning formulations provides identical results.

It will be understood that other formulations involving the compounds of this invention provide the benefits described herein and are within the scope of this invention.

What is claimed is:

1. The quaternary ammonium salt of a para-dialkylamino benzamide having the formula

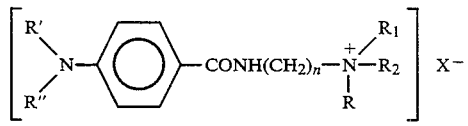

wherein R′ and R″ are each selected from the group of $C_1$ to $C_2$ alkyl; n is an integer having a value of from 2 to 6; R is an alkyl radical having from 1 to 30 carbon atoms; $R_1$ and $R_2$ together with the attached cationic nitrogen atom can form a 5 to 6-membered heterocyclic ring selected from the group of

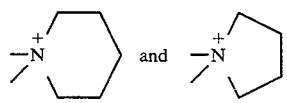

and X is an anion.

2. The quaternary salt of claim 1 wherein R is alkyl having 12 to 18 carbon atoms.

3. The quaternary salt of claim 1 wherein said anion is selected from the group of chloride, bromide sulfate, sulfonate, haloacetal and p-tolyl sulfonate.

4. The quaternary salt of claim 1 wherein said salt is in crystalline form and contains between about 1 and about 8 wt. % moisture.

5. The quaternary salt of claim 1 which is dodecyl-[2-(p-dimethylaminobenzamido)ethyl]-pyrrolidinium bromide.

6. A sunscreening composition containing a carrier and an effective sunscreening amount of a quaternary ammonium salt of a para-dialkylamino benzamide of claim 1.

7. The sunscreening composition of claim 6 wherein a mixture of said quaternary ammonium salts of para-dialkylamino benzamides are employed.

8. The composition of claim 6 wherein said sunscreen is dodecyl-[2-(p-dimethylaminobenzamido)ethyl ]pyrrolidinium bromide.

9. The sunscreening composition of claim 6 which additionally contains one or more of the components selected from the group of a surfactant, a neutralizer, a stabilizer, a propellant, a coloring agent, a fragrance, a film forming polymer, a preservative, an antistat and a sequestrant.

10. The composition of claim 6 which is in admixture with a conventional hair or skin treating formulation.

11. The composition of claim 6 which is in admixture with a paint formulation.

12. The quaternary salt of claim 1 wherein n has a value of from 2 to 4 and R is alkyl having from 12 to 18 carbon atoms.

13. The quaternary salt of claim 12 wherein said heterocyclic ring is a pyrrolidinium ring.

* * * * *